US008734647B2

(12) United States Patent
Bresciani et al.

(10) Patent No.: US 8,734,647 B2
(45) Date of Patent: May 27, 2014

(54) PROCESS FOR THE BIOLOGIC TREATMENT OF ORGANIC WASTES AND PLANT THEREFOR

(75) Inventors: Paolo Bresciani, Canonica D'Adda (IT); Andrea Manfredini, Milan (IT); Andrea Peri, Cusago (IT); Federico Peri, Cusago (IT); Mario Peri, Rivolta d'Adda (IT); Vanessa Pizzaballa, Fara Gera d'Adda (IT); Martino Pretalli, Truccazzano (IT); Antonio Tabarelli, Pozzolo (IT); Antonio Trilli, Magliaso (CH)

(73) Assignee: Bioenergia S.r.l., Milan (IT)

( * ) Notice: Subject to any disclaimer, the term of this patent is extended or adjusted under 35 U.S.C. 154(b) by 26 days.

(21) Appl. No.: 13/320,638

(22) PCT Filed: May 17, 2010
(Under 37 CFR 1.47)

(86) PCT No.: PCT/IB2010/052185
§ 371 (c)(1),
(2), (4) Date: May 1, 2012

(87) PCT Pub. No.: WO2010/131234
PCT Pub. Date: Nov. 18, 2010

(65) Prior Publication Data
US 2012/0264180 A1    Oct. 18, 2012

(30) Foreign Application Priority Data

May 15, 2009  (IT) .............................. MI2009A0861
May 14, 2010  (IT) .............................. MI2010A0866

(51) Int. Cl.
*C02F 3/30* (2006.01)
(52) U.S. Cl.
USPC ........... 210/603; 210/605; 210/615; 210/151; 210/259; 210/903; 210/906

(58) Field of Classification Search
USPC ......... 210/603, 605, 612, 613, 621, 622, 623, 210/629, 630, 252, 259, 903, 906
See application file for complete search history.

(56) References Cited

U.S. PATENT DOCUMENTS 4,315,823 A * 2/1982 Witt et al. .................... 210/605
5,540,839 A  7/1996 Pirt
(Continued)

FOREIGN PATENT DOCUMENTS

DE  10 2006 030773      1/2008
FR      2684094 A *  5/1993
(Continued)

OTHER PUBLICATIONS

Machine-generated English translation of JP 9-108672. Printed on Jun. 11, 2013.*

(Continued)

*Primary Examiner* — Fred Prince
(74) *Attorney, Agent, or Firm* — Young & Thompson

(57) ABSTRACT

Process for the biological treatment of organic wastes, includes a first anaerobic digestion phase and a second aerobic digestion phase in succession, a respective filtration phase of the solid substance being provided between the two digestion phases, a separation phase of the biogas released in the anaerobic digestion phase and a nitrogen recovery phase from the exhaust gases rich in ammoniac substances separated from the aerobic digestion phase. The solid substance coming from each of the filtration phases is separately returned to the respective digestion phase, while the liquid phase coming from the filtration phase downstream of the anaerobic digestion phase is sent to aerobic phase. In the nitrogen recovery phase the gaseous current consisting of exhaust gases rich in ammoniac substances is treated with a solution of carbonic acid supplied in countercurrent in a first gas/liquid contactor to obtain a mixture of nitrogen salts (ammonium bicarbonate, ammonium carbonate, etc.).

18 Claims, 4 Drawing Sheets

(56) References Cited

U.S. PATENT DOCUMENTS

| | | | | |
|---|---|---|---|---|
| 5,578,214 | A * | 11/1996 | Yamasaki et al. | 210/650 |
| 5,798,044 | A * | 8/1998 | Strohmeier et al. | 210/605 |
| 5,932,099 | A * | 8/1999 | Cote et al. | 210/605 |
| 5,961,830 | A * | 10/1999 | Barnett | 210/603 |
| 6,013,511 | A * | 1/2000 | Diels et al. | 435/262.5 |
| 7,001,519 | B2 * | 2/2006 | Linden et al. | 210/602 |
| 7,022,296 | B1 * | 4/2006 | Khang et al. | 423/210 |
| 2005/0006305 | A1 * | 1/2005 | Juby et al. | 210/603 |
| 2007/0062231 | A1 | 3/2007 | Spindler et al. | |
| 2008/0156726 | A1 | 7/2008 | Fassbender | |
| 2011/0084020 | A1 * | 4/2011 | Ott | 210/602 |

FOREIGN PATENT DOCUMENTS

| | | |
|---|---|---|
| JP | 57-27198 A * | 2/1982 |
| JP | 9 108672 | 4/1997 |
| JP | 2002 273489 | 9/2002 |
| JP | 20060334472 | 6/2008 |
| WO | 2008/141413 | 11/2008 |

OTHER PUBLICATIONS

International Search Report dated Sep. 6, 2010, corresponding to PCT/IB2010/052185.

* cited by examiner

PROCESS FOR THE BIOLOGIC TREATMENT OF ORGANIC WASTES AND PLANT THEREFOR

FIELD OF THE INVENTION

The present invention concerns a process for the biologic treatment of organic wastes, and in particular a biologic process for the reduction of the chemical oxygen demand (COD) and the mineralisation and recovery of the pollutants therein contained, in particular of carbon dioxide, nitrogen and phosphorus.

The invention also concerns a plant for the actuation of said process.

KNOWN ART

Firstly, for a better understanding of the following description, for the purposes of the present invention, cultivation conditions are defined aerobic when the tension of the oxygen dissolved in the culture ($pO_2$) is not below 5% of the saturation value in air at atmospheric pressure (oxygen sufficiency conditions). Cultivation conditions are defined microaerophilic when the tension of the oxygen dissolved in the culture ($pO_2$) is below 5% of the saturation value in air at atmospheric pressure, but the culture is not anaerobic since a continuous supply of oxygen to the culture is ensured even if the tension thereof in the liquid cannot be detected by the probe (oxygen limitation conditions).

The treatment of wastes is a strongly felt problem in the majority of developed countries, due to the fact that the eutrophication of inner waters is causing remarkable environmental and economic problems, especially in the areas with high tourist impact. Of particular interest to sector workers are the treatment systems of organic waste of various origin, such as for example those of the agro-food industry and civil wastewaters.

Among these, the zootechnic sector has recently become particularly critical, since the limiting factor for farm size is the availability of ground where to spread wastewaters, consisting mainly of animals' dejections. It is equally known that, on the other side, the profitability of the farming business requires that larger farms are preferred due to the evident economies of scale which can be obtained compared to small-sized ones. On the wave of this economic analysis particularly vast farms have hence been accomplished—in Europe pig farms provide up to 10,000 animals—with a resulting pressure on the ecosystem and relative problems particularly difficult to solve even in the short term. Therefore, various countries have preferred to legislate in the matter putting limitations to the amount of zootechnic wastes which may spread per year per surface unit. For example, in Europe a spreading limitation has recently been introduced based on the nitrogen contents of wastes, virtually reducing the size of pig farms; of course this has a greater impact in the areas with a high farm density, such as for example the Po valley in Italy, Denmark, the Netherlands or Germany.

In addition to following these limitations, pig farms must meet legal requirements concerning the storing of dejections for a sufficient period of time between the end of a spreading season and the beginning of the subsequent one. Such storages normally consist of open tubs wherefrom the gases produced by the substantially anaerobic metabolism of the microorganisms found in the dejections are released in the atmosphere, generally obligate anaerobes, facultative anaerobes and archaebacteria such as methanogens. Since the gases released in the atmosphere comprise gases which contribute to the greenhouse effect, such as methane, carbon dioxide and ammonia, and toxic gases, such as hydrogen sulphide, it can be understood that the storage of wastes implies not irrelevant management problems. Moreover, following this degradation phase, nitrogen-containing substances are obtained, the release of which into the natural environment causes the eutrophication of water bodies and the increase of nitrate level in waters.

It has therefore become necessary to find new processes apt to reduce the amounts of toxic substances, or harmful for the environment, which are freely released into the environment. Especially in northern Europe it has thus been opted for exploiting the chemical energy found in wastes, providing the anaerobic digestion of pig dejections in bioreactors of various configuration, wherefrom biogas is recovered consisting of methane produced in a mixture with carbon dioxide.

The most widespread configurations are continuous-flow stir-tank reactors CSTR (Continuous Stirred Tank Reactor), piston-flow reactors (PFR), fluidised-bed reactors (FBR) and, finally, simple unstirred tubs. Digestion is carried out most frequently in mesophilic conditions (30-40° C.), more rarely in thermophilic conditions (50-60° C.) or psychrophilic (10-20° C.).

In these first experiences it was possible to detect that an element which remarkably reduces dilution speed—theoretically defined as the specific growth speed of the microorganisms found in the bioreactor when it operates in a stationary condition—is the microorganisms' low maximum growth speed, in particular of methanogenic bacteria.

Moreover, it has been detected that the low degradation speed of some wastes components, mainly vegetable fibres, especially if lignified, determines an extension of the residence time of the slurries before they are sufficiently degraded. As can be easily understood, this limitation is generally more restrictive than the first one, and hence makes it necessary to find a solution which shortens the residence time it effectively takes.

In order to overcome this limitation, or at least mitigate the effects thereof, it is usually provided to recycle to the bioreactor part of the biomass therein produced, subject to thickening in a sedimentation tank: thereby, the residence time of biomass and of the other sedimentable particulates becomes longer than the hydraulic residence time, in fact extending the permanence thereof in the reactor. This operation mode, generically known as anaerobic contact digestion, allows a reduction of the work volume of the digester and hence of the investment and running costs, mainly those for heating and stirring.

However, although this process partly solves the problem, it must be kept into consideration that also the sedimentation tank necessary for this operation mode is a reactor which must be of a size proportioned to the residence time of the digester effluent necessary to obtain the desired sedimentation degree. Said residence time is therefore critically dependent on the sedimentability features of the solids, and consequently on the capacity of microbial populations to form relatively stable aggregates capable of sedimenting at appreciable speeds.

Since these phenomena are little known and hard to control, as well as being subject to the unforeseeable composition variations of the incoming slurry, it is easy to understand how this process is rather complex to manage. Although devices are known to reduce residence times and make the plant efficient, known approaches are still based on microorganisms' behaviours hard to control and to reproduce.

EP 0 641 296 describes a degradation procedure of organic material which provides the organic material to alternately and periodically undergo mesophilic and thermophilic digestion. In the mesophilic phase, which is carried out in anaerobic conditions in a suitable reactor, the organic material is at least partly digested with the simultaneous production of mesophilic and anaerobic biomass, while in the subsequent aerobic thermophilic or microaerophilic phase the residual organic material and the biomass of the mesophilic microorganisms coming from the previous phase are at least partly digested. Said cyclical treatment is carried out using the effluent of the aerobic bioreactor as supply for a second anaerobic reactor and so on for a series of reactors. The process is made to continue until the organic material is substantially fully converted into gaseous degradation products and into water. However, the degradation products still have a polluting load which nevertheless raises concerns.

SUMMARY OF THE INVENTION

A first object of the present invention is hence to accomplish a degradation process of organic substances which substantially reduces the polluting load, generating degradation products having low environmental impact, and a plant wherein such process can take place in a simple and effective manner.

In particular, the removal of nitrogen-containing substances from wastes of any origin is an important function of biological treatment systems and the majority of modern plants provides sections therefor: these are typically base on microbiological nitrification/denitrification processes the function of which is the transformation of ammonia into molecular nitrogen which is then released into the atmosphere. This approach has a virtually null environmental impact, but has the disadvantage of bringing nitrogen back to a form not directly usable by vegetables, i.e. a form which requires a prior chemical or biological reduction by nitrogen-fixing microorganisms. As a matter of fact, the chemical reduction with hydrogen which leads to the formation of ammonia (Haber-Bosch process) is the base of the manufacture of nitrogen fertilisers containing ammonium salts and of nitrogen-containing ones, which are typically obtained from ammonia by catalytic oxidation with oxygen (Ostwald process). The nitrification/denitrification processes hence destroy a resource (ammonia) the regeneration of which for use in agriculture requires a considerable energy waste. As a matter of fact, about 80% of the ammonia produced, in the order of 150 million tons/year, is used in agriculture both in the form of ammonium salts and in the form of nitrates derived from said ammonia.

A number of processes are known in the art for ammonia removal from wastes of various origins. For example, US2008/156726 A1 describes the use of basic compounds to shift the balance ammonia/ammonium towards ammonia, thereby facilitating the removal thereof in air and steam stripping systems, while JP2006334472 describes a similar system wherein the solution containing ammonia in the form of ammonium salts is brought to a pH above 8 by adding a base and then it is introduced into a gas/liquid contactor (scrubber) into which air is let in which removes the gaseous ammonia thus generated. Such ammonia is then recovered in a second scrubber fed with an acidic solution. US2007/0062231 A1 describes a method consisting in the heating of the ammonia-containing waste under partial vacuum and in the subsequent absorption of ammonia and of carbon dioxide released during the gaseous phase through a suspension of calcium sulphate; said sulphate is converted into calcium carbonate, which precipitates, and into ammonium sulphate in solution which is then recovered.

However, all known alkalinisation methods provide the shift of the balance towards ammonia by adding a chemical agent deliberately introduced in the system, with evident problems of additional costs for the raw material and of disposal of the reaction by-products.

A second object of the invention is hence to accomplish an innovative process for the mineralisation and the recovery of the nitrogen found in the by-products of the above described biological waste treatment process, playing on the action of the biological agents already present in the bioreactor, selected by the applied operation conditions, so as to obtain nitrogen in high-purity inorganic forms, virtually undistinguishable from those found in commercial chemical fertilisers, with the valuable additional benefit of a cost reduction of nitrogen fertilisation.

Moreover, the eutrophication effect of phosphorous on water bodies is well-known and well documented: particularly felt is hence the need to find processes apt to favour the removal of this element from the waters coming from the treatment of wastes of various origin. Two main phosphorous-removing processes from wastes are currently known: immobilisation in the bacterial biomass, or chemical insolubilisation.

However, in the case of immobilisation, a simple shift of the eutrophying substances from the waste to the sludge is determined, and consequently the further treatment of the sludge is necessary, now consisting of the organic substance with a potential pollutant.

In the case of insolubilisation, it is known to chemically remove the soluble orthophosphate from the wastewaters through processes which use chemical compounds capable of reacting with the orthophosphate originating insoluble compounds which can then be mechanically separated from the waste; however, such compounds are unusable in the agro-food sector, since they have undesired effects on agricultural soils. Moreover, it is also known to make the phosphorous loads contained in the wastes insoluble by converting the orthophosphate into hydroxyapatite ($Ca_5(PO_4)_3(OH)$), a compound which is compatible with agricultural use, but the process is economically convenient only in large plants, given the severe plant complications it implies.

Another object of the present invention is hence that of mineralising to the greatest possible extent the phosphorus found in the incoming slurry, converting it to the largest possible extent to a soluble inorganic form, such as orthophosphate, which can be treated and separated from the sludge with such a purity level to allow its direct further use, for example as fertiliser.

Another object again of the present invention is then that of accomplishing a reduction process of the $CO_2$ released during the above wastewater treatment process, to meet the requirements of greater attention to the release into the atmosphere of gases responsible for the greenhouse effect.

Finally, up until toady, the common problem of all wastewater anaerobic digestion systems is that of the partial removal of the polluting load, for example expressed as COD: as a matter of fact, at the moment, in the common anaerobic digesters operating on piggery wastes the residual COD values range between 35% and 70% of the value found in the incoming waste. The organic substance residues substantially consist in reluctant organic compounds and microbial biomass, which often cannot be released directly into the environment, with the need to carry out further treatments before the release of the effluents into the environment, with a rise of disposal costs and considerable logistic problems, which often cause a further rise of disposal costs.

A further object of the present invention is hence to accomplish a waste treatment which allows to drastically reduce the COD and to make disposal procedures less complex.

BRIEF DESCRIPTION OF THE DRAWING FIGURES

Further features and advantages of the invention are in any case more evident from the following detailed description of a preferred embodiment of a plant wherein to actuate the invention process, wherein the waste is a slurry of a pig farm, given purely as a non-limiting example with reference to the enclosed drawings, wherein.

Figure 1:
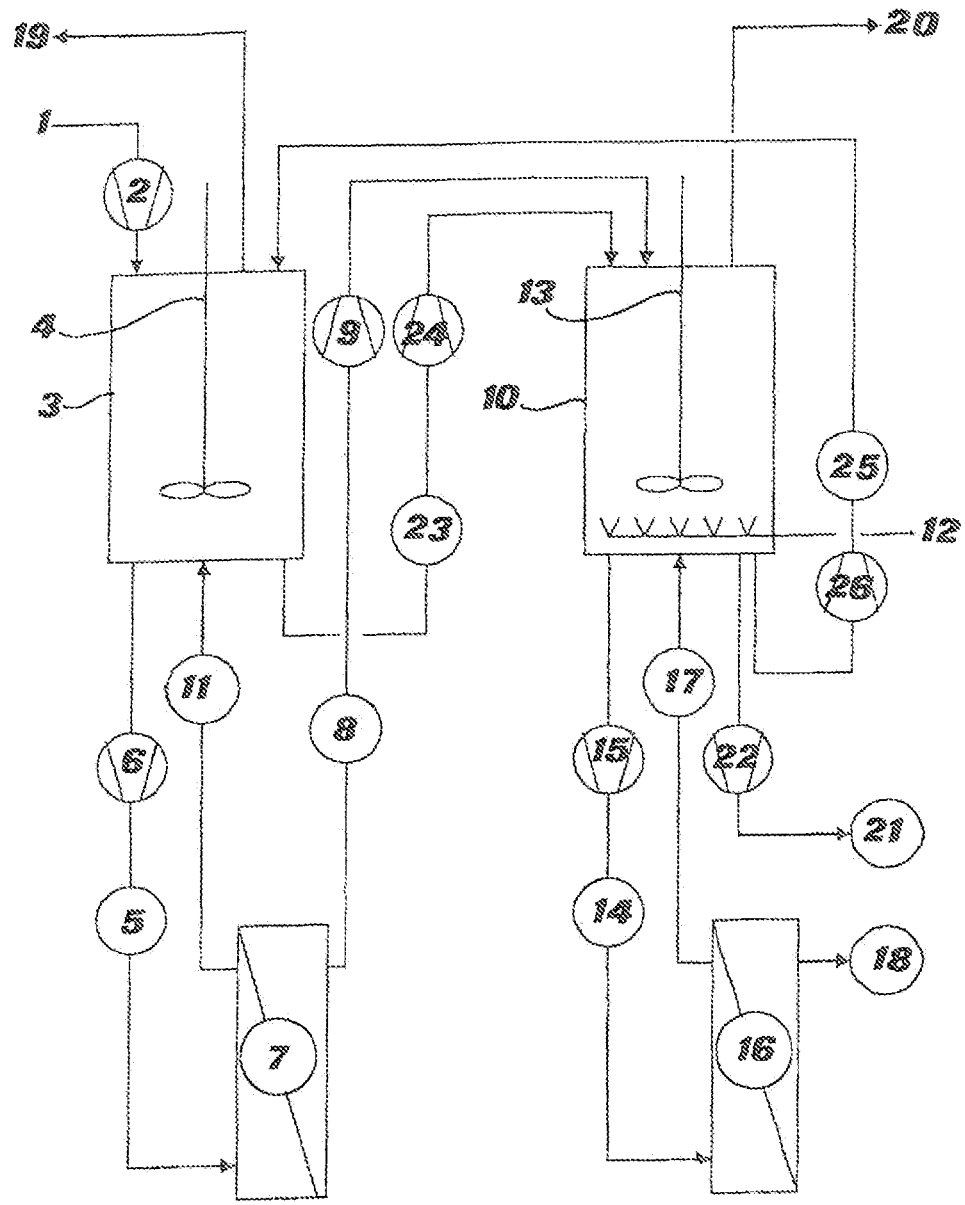
FIG. 1 is a schematic view of a first fraction of the biodegradation plant according to the waste treatment invention in an anaerobic digestor associated with an aerobic digester.
Figure 2:
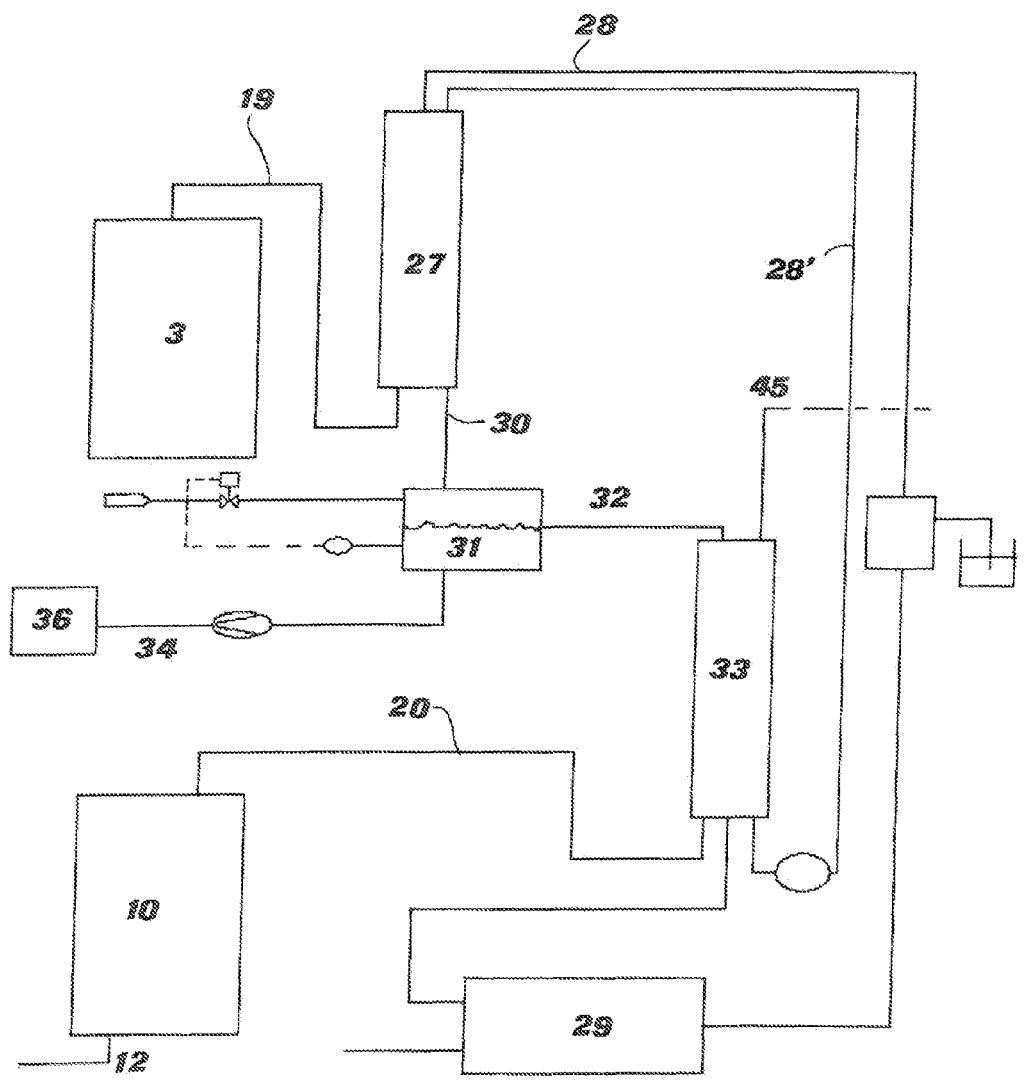
FIG. 2 is a schematic view of a second fraction of the biodegradation plant according to the invention for the treatment of the gaseous effluents coming from the above said digesters for the recovery of nitrogen-containing substances.
Figure 3:
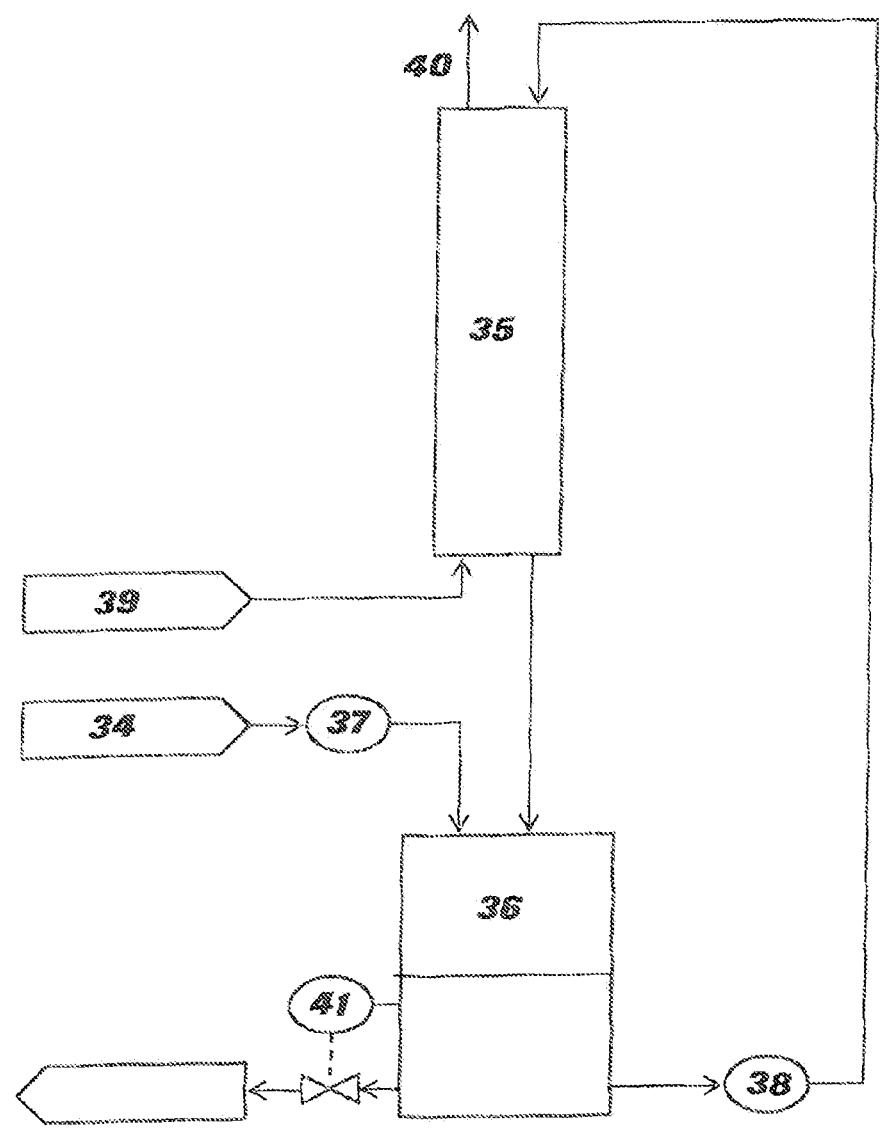
Figure 4:
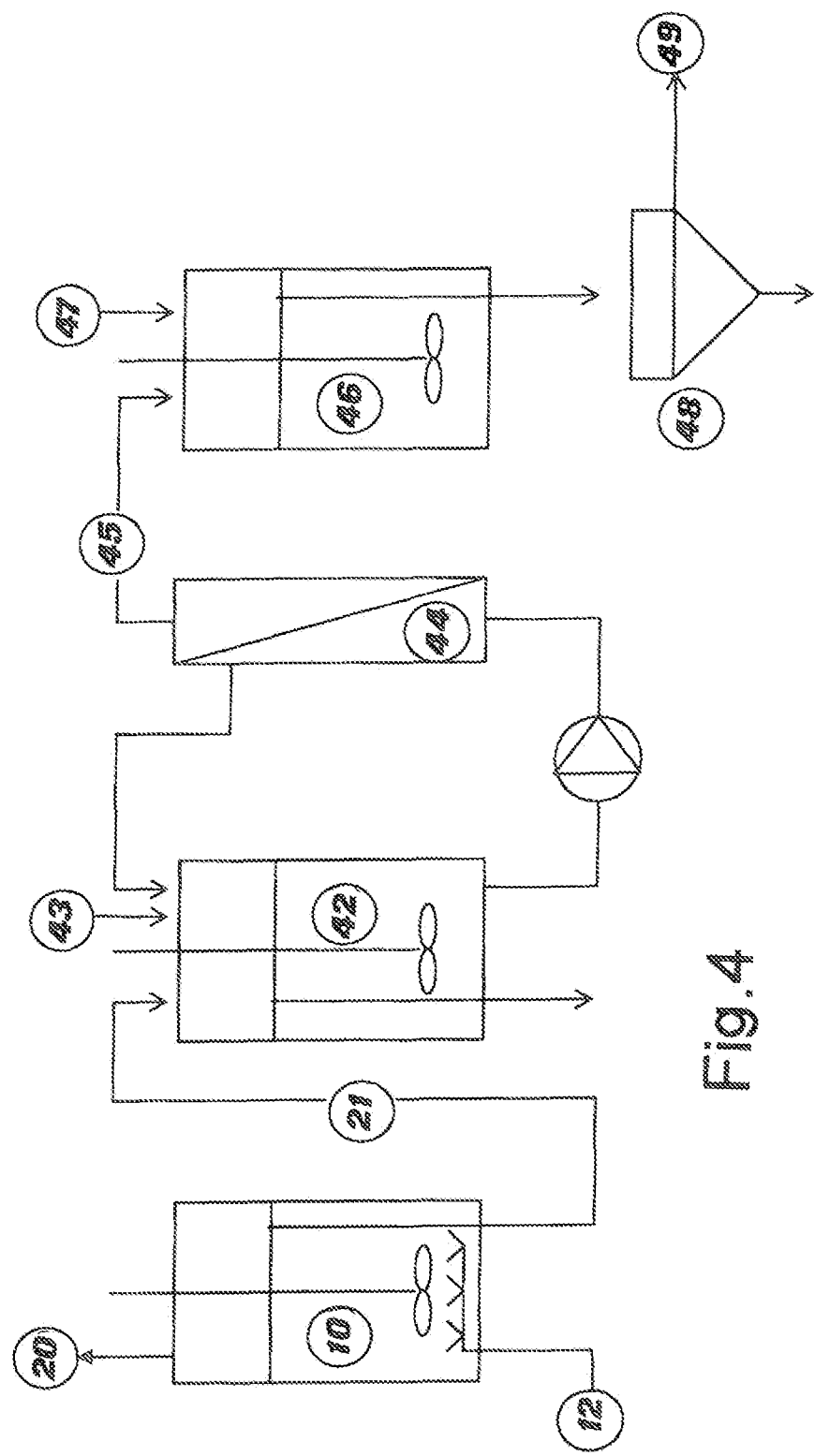

FIG. 3 is a schematic view of a third fraction of the biodegradation plant according to the invention for the treatment of the liquid effluent coming out from the plant fraction shown in FIG. 2, for the partial nitrification of said nitrogen-containing substances; and FIG. 4 is a schematic view of a fourth fraction of the biodegradation plant according to the invention for the treatment of the liquid effluent of the aerobic digester, for phosphate recovery.

The description of the biodegradation plant of the invention will be made, for greater clarity, in connection with the path and the subsequent processing steps which the organic waste undergoes therethrough.

DETAILED DESCRIPTION OF THE INVENTION

A pipe 1, the flow rate of which is adjusted by a supply pump 2, carries the incoming slurry to an anaerobic digester 3, provided with a stirring system 4. The slurry is processed here a first time by means of a substantially conventional treatment for the methanogenic anaerobic digestion, wherein the degradation of part of the organic matter occurs with the resulting generation of a biogas flow 19.

Digester 3 operates in a continuous mode, i.e. with the continuous or periodic release of fresh organic waste and the continuous or periodic removal of the digested contents. In particular, in addition to the above described continuous digestion technique CSTR use can be made of the so-called repeated fed-batch technique (RFB), which provides constant supply and the maintenance of a volume in the reactor ranging between a minimum value and a maximum value, once reached which the liquid volume is discharged in the amount necessary to bring the reactor back to the minimum value of the volume of contained liquid. Typically, in the anaerobic digester 3 the running temperature is maintained in the mesophilic range (30-40° C.).

Whatever the digestion process used, the effluent is brought from the anaerobic digester 3 to a microfiltration apparatus or microfilter 7, through a conduit 5, the flow rate of which is adjusted by a second pump 6. Microfilter 7 acts so as to increase the concentration of suspended solids found in the slurry during the treatment in digester 3.

From microfilter 7, a flow of filtered substance substantially free from suspended solids comes out through a conduit 8, the flow of which is adjusted by a pump 9, to be sent to aerobic or microaerophilic bioreactor 10 for further treatment. At the same time, the solid substance which has been concentrated by filtration by microfilter 7 is instead sent back to digester 3 through a conduit 11, for it to be further treated according to the above described technique.

Bioreactor 10 operates in thermophilic conditions (40-70° C.) and in conditions of sufficient oxygen or of micro-aerophilicness. Such conditions, required for the correct operation of the bioreactor, are obtained by blowing into the bioreactor air or other oxygen-containing gas, through conduit 12, preferably together with mechanical stirring by propellers or turbines 13, so as to increase the oxygen decomposition speed.

In order to verify in real time oxygen concentrations, the tension of the oxygen dissolved in the liquid is measured by means of a conventional galvanometric or polarographic probe (not shown).

Bioreactor 10 operates in a continuous mode with a scheme similar to the mesophilic anaerobic digester. In particular, a conduit 14 departs therefrom comprising a circulation pump 15 which leads the effluent of bioreactor 10 to a second microfiltration apparatus or microfilter 16. The solid substance which does not pass such microfilter is sent back—through a conduit 17—to the same bioreactor 10, while the filtered fluids are brought outside this plant fraction through a conduit 18, for the possible subsequent use. Since the fluid coming out of conduit 18 is a clear solution, free from suspended solids, it is possible to provide—as an alternative to the traditional spreading thereof on fields—a further treatment of said liquid substance so as to turn it into a liquid fertiliser for commercial use.

Moreover, from bioreactor 10 the flow of exhaust gas from slurry treatment is released—through an exit conduit 20—substantially consisting of ammonia substances which prove useful subject to suitable treatment as described below. Finally, the optimal filling level of bioreactor 10 is controlled through a conduit 21 for the outflow of the digested fluid, adjusted by a drawing pump 22. The fluid coming out of conduit 21 is a suspension of solid substances, consisting in particular of microbial biomass and undigested, insoluble solids, and therefore it is normally used exclusively as dung to be spreaded on the ground. According to the process of the present invention, on the contrary, this flow is further treated—as described in detail in the following—to obtain full phosphate removal, so as to allow waste disposal into the water bodies without causing eutrophication phenomena in the same whatsoever. The process of the invention is hence particularly useful in all those cases in which the spreading of treated fluids across agricultural land is not possible, either because the farm does not have the necessary amount of land, or because the phosphate level in the same has already reached excessively high values.

Finally, between digester 3 and bioreactor 10 there are provided two connection pipes, of supply 23, the flow of which is adjusted by a pump 24, and of return 25, respectively, the flow of which is adjusted by a pump 26: the flow through conduit 23 is used—in a way known per se—to keep substantially constant the volume inside digester 3, while the flow through conduit 25 is adjusted so as to obtain the desired recycling intensity. The constancy of the above-said flows in time allows to maintain the entire plant in stationary operating conditions.

As stated above, in a second plant fraction shown in FIG. 2, the gaseous effluents of the first fraction are then treated so as to recover the nitrogen contained in the same and, in a preferred embodiment of the process of the invention, also the carbon dioxide found in the biogas flow 19.

This second plant fraction, apt to further treat the exhaust gases rich in ammoniac substances coming out of exhaust gas conduit 20, schematically consists of a gas/liquid contactor 33, into the lower part of which said conduit leads, wherein the ammonia-containing gaseous phase is put in contact with an acidic solution fed in countercurrent through conduit 32.

The ammonia found in the gaseous phase dissolves into the liquid phase tending to establish a balance with the ammonia dissolved in the liquid. Said ammonia, in turn, establishes a balance with the ammonium ion in solution according to the following reaction:

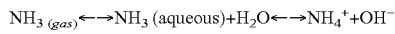
$$NH_3\ (gas) \longleftrightarrow NH_3\ (aqueous) + H_2O \longleftrightarrow NH_4^+ + OH^-$$

The presence of acid neutralises the $OH^-$ ions produced by the reaction, shifting rightwards the balance between the dissolved ammonia and the ammonium ion, hence determining a progressive salification of the ammonia dissolved in the liquid, and thus generating a solution of the ammonium salt of the acid used.

Traditionally, for this acidification operation sulphuric acid may be used and the addition of such acid to the liquid phase supplied to gas/liquid contacter 33 may be advantageously performed by means of an automatic titration apparatus, by which it is provided to keep the pH constant around a preset value, through a probe immersed in the liquid phase.

In the preferred embodiment of the process of the invention, the acid used is instead carbonic acid and such acid is obtained through the washing of the biogas produced by digester 3 through the liquid flow taken at the bottom of gas/liquid contacter 33, with the further advantage of recovering most of the $CO_2$ found in the biogas and hence substantially avoiding the release thereof into the atmosphere. For this purpose conduit 19, which comes from bioreactor 3, supplies the biogas produced in said reactor to a gas/liquid contactor 27 where the biogas is treated in countercurrent through a liquid flow coming from tank 31 through conduit 32, contacter 33 and conduit 28'. Initially such flow consists of water into which hence the $CO_2$ contained in the biogas partly dissolves, until it reaches condition of equilibrium with carbonic acid which, partly dissociating, determines a drop of the pH of such liquid phase.

The biogas, thus poor in $CO_2$, and hence consisting virtually entirely of methane, is extracted from contacter 27 through a conduit 28 and sent to a thermal motor/engine 29, which can be for example a burner, an internal combustion engine, or a turbine motor. The thermal or mechanical energy thus generated by the combustion of the biogas purified from $CO_2$, is favourably used for the internal requirements of the plant, thus improving the energy balance thereof, which the exhaust gases produced by such combustion are partly or fully supplied to the base of gas/liquid contacter 33 so that the $CO_2$ therein contained is absorbed into the liquid phase coming from tank 31, thus bringing a further acidity to the liquid flow of contacters 27 and 33.

The acidic liquid phase coming out from contacter 27, through a conduit 30, also goes to feed a tank 31 which in turn replenishes—through a conduit 32—gas/liquid contacter 33 for the treatment of the gaseous flow of ammonia-containing substances, a flow released by bioreactor 10. The ammonia-containing substances dissolve in the acidic liquid phase coming from tank 31 and their basicity is at least partly neutralised by the acidity introduced in the liquid phase by the $CO_2$ dissolved in contacters 27 and 33. The result of this neutralisation is the formation of a mixture of nitrogen salts (ammonium bicarbonate, ammonium carbonate, etc.) the equilibrium of which is influenced by the pH of the solution.

In order to keep a constant concentration of this mixture of nitrogen salts within tank 31 a top-up water inflow conduit is provided as well as a conduit 34 for the outflow of the solution of nitrogen salts which is stored in a tank 33 for the subsequent stabilisation treatment.

The stabilisation treatment of the mixture of nitrogen salts collected in tank 36 is performed in the third fraction of the plant, shown in FIG. 3. The stabilisation of such mixture is essential because otherwise it would tend to decompose also at relatively low temperatures, generating $NH_3$ and $CO_2$ gas and making it substantially impossible to preserve it for extended periods of time. It is then necessary to proceed to the transformation into nitrate ion of half (in molar terms) of the ammonium found in the solution coming from the system of combined contacters 27 and 33, so as to obtain an aqueous solution of ammonium nitrate ($NH_4NO_3$), a substance having excellent fertilising characteristics, due both to the high percentage content of nitrogen (35% by weight) and of the stability thereof at the solid state or in solution.

The transformation of part of the ammonium ion into nitrate ion occurs biologically through the so-called nitrification reaction, typical of consortiums of microorganisms belonging to the genera *Nitrosomonas, Nitrosococcus* and *Nitrobacter*. The microorganisms belonging to the first two genera oxidise the ammonium ion to nitrite ion using molecular oxygen as electron acceptor, while those belonging to the third genera oxidise the nitrite ion to nitrate ion operating similarly, due to their autotrophy, i.e. their ability to use $CO_2$ as a source of carbon. The high concentration of $CO_2$ in the solution coming from the combined contacter system is hence particularly favourable for the development and the activity of these microorganisms for the purposes of the present invention.

The partial nitrification of the ammonium ion is performed in a bioreactor, containing the nitrifying biomass in liquid suspension or adhered to a solid substrate, which is fed continuously or intermittently with the solution coming from the system of gas-liquid contacters, i.e. with the flow 34 shown in FIG. 2. The chemical compounds necessary for the growth of the nitrifying microorganisms (phosphorus, sulphur, magnesium, diverse oligo-elements) are fed to the system in the form of a suitable salts solution or more simply as fresh slurry added in a suitable amount to the solution of ammonia salts (34).

FIG. 3 schematically shows such a nitrification system wherein the nitrifying biomass is contained in a bioreactor 35 consisting of a cylindrical container filled with a suitable material which retains the nitrifying biomass on its surface or within cavities of the material. The immobilised-biomass bioreactor is fed continuously or intermittently with the solution of ammonia salts 34 contained in a tank 36 into which it is poured through a pump 37 and from which it is drawn by a pump 38 which sends it to the head of bioreactor 35. The solution percolates through the bioreactor coming in contact with the nitrifying biomass contained therein and is hence collected again in tank 36. A continuous circulation of the solution of ammonia salts through bioreactor 35 is hence accomplished, which brings such salts continuously in contact with the nitrifying biomass and determines a progressive transformation of the ammonium ion into nitrate ion.

In order to favour said transformation, bioreactor 35 is fed with air, or other oxygen-containing gas, which is delivered into the lower part (flow 39) and is released in the top part (flow 40). The progressive increase of the concentration of nitrate ions and the corresponding decrease of the concentration of ammonium ions in the liquid contained in container 36 can be controlled by continuously or periodically delivering a fresh solution of ammonia salts 34 through pump 37 and the simultaneous removal of nitrified solution by using a system for the automatic level control which keeps the volume constant by actuating a valve 41 for the outflow of a liquid flow from tank 36. In principle it is possible to maintain the concentration ratio of ammonium ions and nitrate ions at a preset value by acting on the addition velocity of the former ones and the removal of the latter ones, once the nitrification velocity in bioreactor 35 is known.

Based on the dynamic balance of the two chemical species being examined in the system shown in FIG. 3 it is easy to show that the ration between the two species, defined as:

$$R=[NH4]/[NO3] \quad (1)$$

varies depending on the feeding flow of fresh solution to the tank (36) according to the equation $$R=D[NH4]in/(D\,[NH4]in-r)-1 \quad (2)$$

where: [NH4]=concentration of ammonium ions (moles/L)
  [NH4]in=concentration of ammonium ions in the feeding flow (moles/L)
  [NO3]=concentration of nitrate ions (moles/L)
  D=F/V
  F=feeding flow (L/h)
  V=total volume of the liquid in the nitrification system (L)
  r=volumetric velocity of transformation of ammonium into nitrate (moles/L h)

Of course, the volumetric velocity of transformation of ammonium into nitrate (r) is not a constant, but depends, among other things, on the amount of nitrifying biomass and on the concentration of ammonium and nitrate ions in the system. In its simplest form such dependence may be expressed by a function of the Michaelis-Menten type, i.e.

$$r=qm \times S/(S+Ks) \quad (3)$$

where: qm=maximum nitrification velocity for biomass unit (moles/g h)
  X=total amount of nitrifying biomass in the system (g)
  S=concentration of ammonium ion in the liquid (mol/L)
  Ks=saturation constant (mol/L)

The combination of Eq. (2) with Eq. (3) gives a relationship between parameter D (specific feeding velocity) and variable s (residual concentration of ammonium ion in the system). It is easy to show that for each value of D a single value of S corresponds. The relationship is such that very high values of D determine an excess of ammonium ion compared to the nitrate ion, while very low values of D lead to the opposite situation. It is hence evident that a value of D exists which in correspondence of which the parameter R defined in Eq. (1) takes on the value of 1, corresponding to an aqueous solution of ammonium nitrate. Such value of D is given by the expression $$D=2\,r/[NH4]in \quad (4)$$

In the fourth and last fraction of the plant according to the present invention the recovery of inorganic phosphorus is finally carried out, which is found among the effluents from bioreactor 10 which are taken through conduit 21, in the form of orthophosphate. In order to proceed to the recovery thereof, a system (FIG. 4) is used which consists of the following main units:
  stirred reactor 42 which receives effluent 21 coming from bioreactor 10 and acidifies it by adding an acid 43;
  microfiltration device 44 which operates in recirculation on reactor 42 producing a clear effluent 45;
  stirred reactor 46 which receives clear effluent 45 and determines the precipitation of the phosphate found in effluent 45 through the addition of chemical compound 47;
  filtration system 48 which receives the suspension containing the insoluble compound containing the phosphate coming from reactor 46 and allows the recovery of insoluble compound 49.

The acidification of the effluent of aerobic reactor 10 allows the solubilisation of the phosphate-containing insoluble compounds possibly present in reactor 10 due to the high pH value found therein. Such solubilisation is necessary to allow an efficient recovery of orthophosphate in clear effluent 45 produced by the microfiltration system 44 since any insoluble compounds would be retained by the filtering membrane.

The precipitation of the orthophosphate found in clear effluent 45 is obtained by adding magnesium salts (for example $MgCl_2$, $MgSO_4$, MgO and the like) and the simultaneous alkalinisation of effluent 45. The use of MgO or of $Mg(OH)_2$ is particularly advantageous since it simultaneously determines the addition of magnesium ions and the alkalinisation of the solution. The simultaneous presence of ammonium and of orthophosphate in effluent 45 causes the addition of magnesium salts to determine the precipitation of the compound $Mg(NH_4)PO_4$ (struvite), particularly advantageous in the application as fertiliser for agricultural uses. Said compound can be recovered through a filtration, sedimentation, centrifugation or other equivalent solid-liquid separation operation.

The process described so far is evidently simplified. In particular, it does not take into account some variables which in practice reduce the yield of the plant subject of the invention. As a matter of fact the description has not taken into account the fact that the suspended solids found in the bioreactor do not consist exclusively of biomass formed within the bioreactor starting from a soluble substrate, but also from insoluble substrates which can partly be used for the growth of the biomass in the bioreactor. In general it is nevertheless to be expected that the production of an effluent substantially devoid of suspended solids determines an increase of the biomass concentration in the bioreactor and hence of the volumetric degradation capacity thereof.

The use of microfiltration as a concentration method of suspended solids represents a remarkable improvement over the use of a sedimentation tank, since the efficiency of said tank crucially depends on the sedimentability characteristics of the suspended solids, which characteristics are hardly controllable by the operator. The above-described microfiltration apparatuses 7 and 16 advantageously reduce the complexity and the cost of manufacture and running the plant since it is no longer necessary—like in the known art—to provide within the plant the use of a sedimentation tank and furthermore to actuate all those technical devices necessary to obtain a high sedimentation capacity within reasonable times.

The increase of the concentration of suspended solids in both bioreactors 3 and 10 which form part of the biodegradation plant subject of the present invention determines a remarkable increase of the overall degradation capacity, which in turn translates into a very pronounced decrease of the polluting load, as can be determined based on the overall reduction of the so-called volatile solids, essentially a measure of the organic substance found in the waste, or of the COD.

Such reduction is assessed based on the balance of volatile solids, or of the COD, between waste inflow 1 into the plant and treated waste outflow consisting overall of three flows, i.e. of the flow 18 of the outgoing filtrate from the microfiltration apparatus 16 connected to bioreactor 10, of the flow of concentrated fluid 21 and of flow 20 of exhaust gases going out from the same bioreactor 10. It would be necessary to consider that also flow 19 of the biogas coming out from bioreactor 3 contributes to the overall balance of the COD; however, this source of COD no longer contributes to the polluting work released into the environment since it is used for energy production by combustion or electrochemically through fuel cells.

As far as the recovery phase of ammonia gases produced in the second plant fraction is concerned, contacter 33 preferably operates in a continuous mode, as is clearly described in the final phase of the following example. Of course, the plant could operate also in a discontinuous mode using the same liquid phase until reaching the desired concentration of the ammonium salt.

Operation conditions are chosen base on the desired recovery efficiency of ammonia gases and of the pH value of the contents of bioreactor 10, which must be not below about 8. At this pH value and at the chosen temperature (55° C.) the position of equilibrium between dissolved ammonia ($NH_3$ aq) and ammonium ion ($NH_4^+$) is such that dissolved ammonia represents about 55% of the overall ammonia in solution. Free ammonia in solution tends to establish an equilibrium with the ammonia found in the gaseous phase, consisting of the air 12 blown into bioreactor 10 to maintain the desired aerobic conditions, depleted of oxygen and enriched with carbon dioxide and ammonia during the contact with the liquid phase found in the bioreactor. The continuous delivery of fresh gaseous phase and the corresponding removal of ammonia-enriched gaseous phase hence determine a net removal of gaseous ammonia from bioreactor 10.

EXAMPLE

COD Reduction

In the following an application of the present invention is shown, with reference to the drawings for the identification of the components and of the flows.

An anaerobic bioreactor with a geometric volume of 15 l provided with mechanical stirring device and with a measuring and automatic temperature control device is filled up to a volume of 10 l with waste having the following characteristics:

| | |
|---|---|
| Total solids | 38.7 g/l |
| Volatile solids | 26.3 g/l |
| COD | 52.7 g/l |

The temperature is maintained at 35° C. and stirring at 60 rpm/min. The gas produced is collected in a hydraulic gasometer and measured daily. When the gas production begins to decline after having reached its maximum value, a feeding with fresh waste is started at the flow rate of 500 ml a day, while the volume is maintained constant at 10 l with an overflow device. The resulting dilution velocity is 0.0021 $h^1$, corresponding to an average residence time of 20 days.

When the system reaches a stationary state assessed based on the constancy over time of the concentration of volatile solids, of the effluent COD and of the biogas production and composition, the bioreactor is connected to a microfiltration module equipped with a ceramic membrane with nominal porosity of 100 nm, supplied by a centrifuge pump capable of ensuring a tangential flow within the membrane of 3-4 m/sec. The transmembrane pressure is kept between 0.3 and 0.5 bar by acting on a flow reduction valve arranged downstream of the module on the return line of the retented substance to the anaerobic bioreactor.

The permeate produced by the microfiltration module is sent to an aerobic bioreactor with a geometric volume of 15 l provided with mechanical stirring device, adjustable air blowing-in, temperature measuring and control devices, pH measuring devices and measuring devices of the dissolved oxygen tension. The supply flow rate of the bioreactor is adjusted to 400 ml a day. The effluent of the anaerobic bioreactor, removed from the device for the maintenance of a constant volume, is also sent to the 15-l aerobic bioreactor, which operates at 55° C. and with a constant volume of 10 L. The aerobic condition of the aerobic bioreactor is obtained by means of mechanical agitation by means of Rushton turbines and continuous air blowing in. The maintenance of the aerobic conditions is verified through the measurement of the tension of the dissolved oxygen, which is maintained at values not below 5% of the air saturation value at atmospheric pressure through suitable adjustments of the stirring velocity and/or of the air blowing-in flow rate. The stirring velocity ranges between 100 and 300 rev/min and the flow rate of blown-in air ranges between 1.0 and 1.5 l/min.

The aerobic bioreactor is connected to a microfiltration module similar to the one connected to the anaerobic bioreactor, which operates in the same supply and trans-membrane pressure conditions. The flow rate of the permeate produced by this module is set at 400 ml a day.

The volume of the fluid contained in the aerobic bioreactor is kept at 10 l by means of an automatic level control device which discharges from the bioreactor the excess fluid. Therefore, the overall hydraulic flow rate going out from the aerobic bioreactor consists of the sum of the flow rate of the permeate and of the overflow rate of the excess fluid. Such flow rate is ideally identical to the supply flow rate of the anaerobic bioreactor, but in practice it is smaller than that due to the water loss from the bioreactor through two gaseous flows:

1) outgoing biogas from the anaerobic bioreactor (flow 19);
2) outgoing exhaust air from the aerobic bioreactor (flow 20).

Such water losses at the steam state are minimised, but not entirely removed, through the installation on the spill lines of the two bioreactors of reflux condensers fed with iced water. The water lost in such way is hence missing from the water balance of the system.

In addition to the two outputs mentioned above, i.e. the microfiltration permeate and the excess liquid deriving from the maintenance of the constant volume, a flow of liquid of 50 ml/day is furthermore drawn from the aerobic bioreactor, which is fed to the anaerobic bioreactor.

After a suitable period of time the system reaches a stationary state assessed on the base of the constancy over time of the concentration of volatile solids and of the COD in both bioreactors and in the different liquid flows, in addition to the biogas production and composition.

At this point the supply of the anaerobic bioreactor is gradually increased up to 1000 ml/day, increasing at the same time to the same proportion the flow rate of the permeate of the microfiltration connected to the anaerobic bioreactor which reaches a value of 800 ml/day, the flow rate of the permeate of the microfiltration connected to the aerobic bioreactor which reaches a value of 800 ml/day, and the recycling flow rate from the aerobic bioreactor to the anaerobic bioreactor which reaches a value of 100 ml/day. The overflow rate of the aerobic reactor reaches the value of 180 ml/day. Therefore, the water balance of the entire system lacks 20 ml/day, presumably due to the loss of water steam in the gaseous effluents of the system as discussed previously. In this operation attitude the anaerobic digester operates with a dilution rate (referred to the sole feeding with piggery waste) of 0.00417 h$^{-1}$, corresponding to a hydraulic residence time of 10 days.

After a suitable period of time the system reaches a new stationary state assessed on the basis of the constancy over time of the concentration of volatile solids and of the COD in both bioreactors and in the different liquid flows, as well as of biogas production and composition.

Given the COD balance relationship valid in a stationary state:

$$COD_{in} = COD_{CH4} + COD_{18} + COD_{21} + COD_{cons},$$

Where:
$COD_{in}$: incoming COD
$COD_{CH4}$: COD in the produced biogas
$COD_{18}$: COD present in the filtrate of the microfiltration connected to bioreactor 10
$COD_{21}$: COD present in the effluent of bioreactor 10
$COD_{cons}$: COD removed from the incoming waste;
and given the following values for the individual components:
$COD_{in}$: 52.7 g/day
$COD_{CH4}$: 34.2 g/day
$COD_{18}$: 2.7 g/l
$COD_{21}$: 32.5 g/l
the balance of the COD expressed in g/day becomes:

$$52.7 = 34.2 + 0.8*2.7 + 0.18*32.5 + COD \text{ consumption}$$

wherefrom it is evinced that the COD reduction net of the methane production in the combined system is of 10.49 g/day. The outgoing COD from the plant net of the methane production is of 8.0 g/day, which corresponds to a COD reduction of 84.8%. The efficiency of the conservation of the COD found in the waste in the produced methane is 64.9%. During the observation period the total COD contents in the system consisting of the anaerobic bioreactor and of the aerobic bioreactor has remained constant, confirming the validity of the hypothesis of stationary state whereon the balance expressed by the equation is based.

The gaseous effluent coming out of the aerobic bioreactor contains 50% of the total incoming nitrogen in the form of ammonia. Such effluent is introduced into a gas/liquid contacter consisting of a column of plastic material filled with cylindrical glass elements (Raschig rings) whereon an aqueous phase is made to percolate introduced into the top part of the column through a circulation pump which takes it from a reserve whereto the solution returns after having passed through the column. The gaseous phase containing ammonia coming from the bioreactor is introduced into the bottom part of the column and hence moves in countercurrent with respect to the aqueous phase. The pH probe connected to the pH amplifier has an adjustment point set at 4.0. The automatic correction of the pH of the liquid in the reserve has been performed by adding a solution of sulphuric acid at 5% (p/v). The consumption of sulphuric acid is determined through the periodic reading of the solution level in the reserve. Such consumption is proportional to the amount of ammonia transferred from the gaseous phase to the liquid phase. Periodically solution samples are drawn from the reserve and the ammonia concentration present as ammonium sulphate is determined through a selective ion probe, or by steam current distillation and acid/base titulation.

The concentration increase of ammonium ion in the reserve of the contact fluid is in perfect accord with the values calculated on the basis of the consumption of sulphuric acid at 5%, which in actual fact is a direct titulation of the ammonia which dissolves in the contact fluid. The increase of the amount of ammonium ion in solution measured in a time frame of 168 h is of 8.5 g, corresponding to the absorption of 6.6 g of ammoniac nitrogen, i.e. 94% of the value calculated on the basis of the nitrogen balance in the liquid phase.

From the above reported description it can be clearly understood how the present invention allows to achieve all the set objects. In particular a degradation process of the organic substances and a plant therefor has been provided, which meet the effectiveness, reproducibility and control requirements employing a concentration technique of the microbial biomass and of the particulates found in the digestion mixture based on tangential microfiltration, wherein the separation between particulate (including microorganisms) and clear fraction does not depend on the microorganisms' characteristics, but on the characteristics of the chosen filtering means and on the imposed operative conditions. Such approach, already employed in MBRs (Membrane Bio-Reactors) used for the aerobic degradation of wastes, has been extended to anaerobic digesters.

The set object has furthermore been achieved through a biological treatment process consisting of a single anaerobic phase and a single aerobic or micro-aerophilic phase in succession. Thereby, the production of biogas is initially favoured to the detriment of nitrogen mineralisation, and subsequently—keeping high the values of pH and temperature—the transformation of organic nitrogen into ammonia/ammonium is obtained for an overall 70% of the original nitrogen. The solution of ammonium salt thus obtained can be employed as mineral nitrogen fertiliser. It has furthermore been achieved to accomplish an innovative process for the mineralisation and recovery of the main substances which determine environmental stress from wastes, such as nitrogen, phosphorus and carbon dioxide, according to the ways described above through a biological process. As a matter of fact the basification necessary for shifting the balance towards ammonia having been obtained through the sole activity of the biological agents found in the bioreactor, selected from the applied operative conditions, starting from agro-food wastes.

The recovery has finally been obtained of the phosphorus present in the incoming waste, in the form of a compound particularly useful in agriculture, $Mg(NH_4)PO_4$ (struvite), which has the advantage of employing part of the substances to be extracted from the waste and to require only the addition of suitable amounts of magnesium salts.

The simplicity of the plant shows that this process is per se applicable also on small scale at the waste-producing farm, such as for example an animal farm.

The invention claimed is:
1. A plant for the biological treatment of organic wastes, comprising:
first and second reactors respectively for the anaerobic digestion (3) and aerobic digestion (10) in succession;
filtration means of the solid substance (7, 16) arranged downstream of each reactor;
means for the separation of biogas which is released in said first reactor;
means for the separation of exhaust gases rich in ammoniac substances from said second reactor; and
means for the mineralisation of the ammoniac substances into nitrogen salts, wherein
the solid substance retained by said filtration means (7, 16) is recycled to the respective reactor while the liquid phase separated by filtration means (7) downstream of the anaerobic digestion reactor (3) is sent to the aerobic digestion reactor (10).

2. The plant as claimed in claim 1, wherein said filtration means are tangential microfiltration devices.

3. The plant as claimed in claim 2, wherein said means for the mineralisation of the exhaust gases rich in ammoniac substances comprise a first gas/liquid contactor (33) to bring into solution said ammoniac substances and a second gas/liquid contactor (27) to extract $CO_2$ contained in said biogas and at least a mixing device of said solutions.

4. The plant as claimed in claim 3, further comprising a thermal engine (29) for plant actuation, supplied with the flow of combustible gas coming out of said second gas/liquid contactor (27).

5. The plant as claimed in claim 4, wherein the exhaust gases of said thermal engine (29) are sent to the bottom of said first gas/liquid contactor (33) to determine a further acidification of the liquid phase.

6. The plant as claimed in Claim 3, wherein there are further provided means for the nitrification of said nitrogen salts, said means for nitrification comprising an immobilised biomass bioreactor supplied with a solution of ammonia salts (34) contained in a tank (36) into which the solution is delivered through a first pump (37) and wherefrom the solution is drawn by a second pump (38) which sends the solution to a head of the biomass bioreactor, said bioreactor (35) being supplied with an oxygen-containing gas.

7. The plant as claimed in claim 3, wherein means for phosphorus recovery are furthermore provided, comprising:
a solubilisation reactor which receives effluent coming from the aerobic bioreactor and acidifies the effluent through addition of an acid;
a microfiltration device which operates in recirculation on said reactor producing a clear effluent and returning separated solid substance to the reactor;
a precipitation reactor which receives the clear effluent and determines the precipitation of the phosphate found in the effluent through addition of a chemical compound; and
a filtration device which receives the suspension containing the insoluble phosphate compound coming from the second reactor and separates insoluble phosphorus compound.

8. A plant for the biological treatment of organic wastes, comprising:
first and second reactors respectively for the anaerobic digestion (3) and aerobic digestion (10) in succession;
a plurality of tangential microfiltration devices (7, 16) arranged downstream of each reactor;
means for the separation of biogas which is released in said first reactor;
means for the separation of exhaust gases rich in ammoniac substances from said second reactor; and
a mineraliser of the ammoniac substances into nitrogen salts, the mineraliser comprising a first gas/liquid contactor (33) to bring into solution said ammoniac substances and a second gas/liquid contactor (27) to extract $CO_2$ contained in said biogas and at least a mixing device of said solutions; and
a nitrification device comprising an immobilised biomass bioreactor supplied with a solution of ammonia salts (34) contained in a tank (36) into which the solution is delivered through a first pump (37) and wherefrom the solution is drawn by a second pump (38) which sends it to a head of the biomass bioreactor, said bioreactor (35) being supplied with an oxygen-containing gas, wherein the solid substance retained by said filtration means (7, 16) is recycled to the respective reactor while the liquid phase separated by filtration means (7) downstream of the anaerobic digestion reactor (3) is sent to the aerobic digestion reactor (10).

9. The plant as claimed in claim 8, further comprising a thermal engine (29) for plant actuation, supplied with the flow of combustible gas coming out of said second gas/liquid contactor (27).

10. The plant as claimed in claim 9, wherein the exhaust gases of said thermal engine (29) are sent to the bottom of said first gas/liquid contactor (33) to determine a further acidification of the liquid phase.

11. The plant as claimed in claim 8, wherein means for phosphorus recovery are furthermore provided, comprising:
a solubilisation reactor which receives the effluent coming from the aerobic bioreactor and acidifies it through the addition of an acid;
a microfiltration device which operates in recirculation on said reactor producing a clear effluent and returning separated solid substance to the reactor;
a precipitation reactor which receives the clear effluent and determines precipitation of the phosphate found in the effluent through addition of a chemical compound; and
a filtration device which receives the suspension containing the insoluble phosphate compound coming from the second reactor and separates insoluble phosphorus compound.

12. A plant for the biological treatment of organic wastes, comprising:
first and second reactors respectively for the anaerobic digestion and aerobic digestion in succession;
a filter of the solid substance arranged downstream of each reactor;
a separator of biogas which is released in said first reactor;
a separator of exhaust gases rich in ammoniac substances from said second reactor; and
a mineraliser of the ammoniac substances into nitrogen salts, wherein
the solid substance retained by said filter is recycled to the respective reactor while the liquid phase separated by the filter downstream of the anaerobic digestion reactor is sent to the aerobic digestion reactor.

13. The plant as claimed in claim 12, wherein said filters are tangential microfiltration devices.

14. The plant as claimed in claim 13, wherein said mineraliser comprises a first gas/liquid contactor to bring into solution said ammoniac substances and a second gas/liquid contactor to extract $CO_2$ contained in said biogas and at least a mixing device of said solutions.

15. The plant as claimed in claim 14, further comprising a thermal engine for plant actuation, supplied with the flow of combustible gas coming out of said second gas/liquid contactor.

16. The plant as claimed in claim 15, wherein the exhaust gases of said thermal engine are sent to a bottom of said first gas/liquid contactor to determine a further acidification of the liquid phase.

17. The plant as claimed in claim 14, wherein there are further provided nitrification device comprising an immobilised biomass bioreactor supplied with a solution of ammonia salts contained in a tank into which the solution is delivered through a first pump and wherefrom the solution is drawn by a second pump which sends the solution to a head of the biomass bioreactor, said bioreactor being supplied with an oxygen-containing gas.

18. The plant as claimed in claim 15, further comprising a phosphorous recover system comprising:
- a solubilisation reactor which receives the effluent coming from the aerobic bioreactor and acidifies the effluent through the addition of an acid;
- a microfiltration device which operates in recirculation on said reactor producing a clear effluent and returning the separated solid substance to the reactor;
- a precipitation reactor which receives the clear effluent and determines precipitation of the phosphate found in the effluent through the addition of a chemical compound; and
- a filtration device which receives the suspension containing an insoluble phosphate compound coming from the second reactor and separates the insoluble phosphorus compound.

* * * * *